United States Patent [19]

Huang et al.

[11] Patent Number: 5,217,879
[45] Date of Patent: Jun. 8, 1993

[54] INFECTIOUS SINDBIS VIRUS VECTORS

[75] Inventors: Henry V. Huang, University City, Mo.; Robin Levis, Takoma Park, Md.; Charles M. Rice; Sondra Schlesinger, both of University City, Mo.; Ping Shen, University City; Cheng Xiong, St. Louis, both of Mo.

[73] Assignee: Washington University, St. Louis, Mo.

[21] Appl. No.: 815,602

[22] Filed: Dec. 27, 1991

Related U.S. Application Data

[63] Continuation of Ser. No. 296,454, Jan. 12, 1989, abandoned.

[51] Int. Cl.$^5$ .................... C12P 21/00; C12N 7/01; C12N 15/86; C12N 5/10
[52] U.S. Cl. ........................... 435/69.1; 435/235.1; 435/240.2; 435/320.1; 435/91; 536/24.1; 935/32; 935/57; 935/76
[58] Field of Search ............... 435/235.1, 320.1, 240.2, 435/172.3, 69.1, 69.2, 91; 935/32, 36, 57, 70; 536/27

[56] References Cited

U.S. PATENT DOCUMENTS

| | | | |
|---|---|---|---|
| 4,719,177 | 1/1988 | Baltimore et al. | 435/91 |
| 4,745,051 | 5/1988 | Smith et al. | 435/69.1 |
| 5,091,309 | 2/1992 | Schlesinger et al. | 435/69.1 |

OTHER PUBLICATIONS

Hertz, J. M. et al., 1992, *J. Virol.* vol. 66 pp. 857–864.
Raju, R. et al., 1991, *J. Virol.* vol. 65 pp. 2501–2510.
Levis, R. et al., 1990, *J. Virol.* vol. 64 pp. 1726–1733.
Schlesinger, S. et al., 1988, In *Current Communications in Molecular Biology Viral Vectors,* Gluzman, Y. et al., Eds. Coldspring Harbor Laboratory, pp. 167–171.
Ou et al., 1982, *Proc. Nat. Acad. Sci. USA,* vol. 79 pp. 5235–5239.
Levis, R. et al., 1986, *Cell* vol. 44, pp. 137–145.
Rice, C. M. et al., 1987, *J. Virol.* vol. 61 pp. 3809–3819.
Abstract form for VIIth International Congress of Virology, by Cheng Xiong.

Pelletier, J. & Sonenberg, N. (1988) Nature 334:320–325 "Internal initiation of translation of eukaryotic mRNA directed by a sequence derived from poliovirus RNA".
Jackson, R. J. (1988) Nature 334:292–293 "Picornaviruses break the rules".
Rice, C. M. et al. (1987) Journal of Virology 61:3809–3819 "Production of Infectious RNA Transcripts from Sindbis Virus cDNA Clones".
Takamatsu, N. et al. (1987) The EMBO Journal 6:307–311 "Expression of bacterial chloramphenicol acetyltransferase gene in tobacco plants mediated by TMV-RNA".
Levis, R. et al. (1987) Proc. Nat'l. Acad. Sci., U.S.A. 84:4811–4815 "Engineered defective interfering RNAs of Sindbis virus express bacterial chloramphenicol acetyltransferase in avian cells".
French, R. et al. (1986) Science 231:1294–1297 "Bacterial Gene Inserted in an Engineered RNA Virus: Efficient Expression in Monocotyledonous Plant Cells".

(List continued on next page.)

*Primary Examiner*—Richard A. Schwartz
*Assistant Examiner*—Mary E. Mosher
*Attorney, Agent, or Firm*—Rogers, Howell & Haferkamp

[57] ABSTRACT

Compositions and methods are disclosed for expressing heterologous coding sequences in host cells. The compositions include infectious Sindbis virus RNA molecules containing at least one heterologous coding sequence inserted within the structural region of the Sindbis virus genome. RNA molecules consisting essentially of a Sindbis virus junction region are also provided. Methods utilizing the novel compositions of the present invention to express heterologous coding sequences in transformed host cells are provided. Methods for producing infectious Sindbis virus particles containing infectious Sindbis virus RNA molecules comprising at least one heterologous coding sequence are provided.

32 Claims, 3 Drawing Sheets

OTHER PUBLICATIONS

Melton, D. A. et al. (1984) Nucleic Acids Research 12:7035–7056 "Efficient in vitro synthesis of biologically active RNA and RNA hybridization probes from plasmids containing a bacteriophage SP6 promoter".

Krieg and Melton (1984) Nucleic Acids Research 12:7057 "Functional messenger RNAs are produced by SP6 in vitro transcription of cloned cDNAs".

Strauss, E. G. et al. (1984) Virology 133:97–110 "Complete Nucleotide Sequence of the Genomic RNA of Sindbis Virus".

Alton and Vapnek (1979) Nature 282:864–869 "Nucleotide sequence analysis of the chloramphenicol resistance transposon Tn9".

Burge and Pfefferkorn (1966) Virology 30:204–213 "Isolation and Characterization of Conditional–lethal Mutants of Sindbis Virus".

Burge and Pferrerkorn (1966) Virology 30:214:223 "Complementation Between Temperature-sensitive Mutants of Sindbis Virus".

INFECTIOUS SINDBIS VIRUS VECTORS

This invention was made with government support under grant numbers AI24134, AI11377 and AG05681 awarded by the National Institutes of Health. The government has certain rights in the invention.

This is a continuation of application Ser. No. 07/296,454, filed Jan. 12, 1989, now abandoned.

TECHNICAL FIELD

This invention relates to self replicating Sindbis virus RNA vectors capable of expressing heterologous coding sequences in host cells transformed with these vectors. In one embodiment, the Sindbis virus RNA vectors comprise infectious Sindbis virus RNA molecules having inserted therein at least one heterologous coding sequence such that the heterologous coding sequence is flanked by Sindbis virus RNA sequences sufficient to provide for the replication and transcription of the heterologous coding sequence in a host cell. In another embodiment, this invention relates to a Sindbis virus junction region comprising an RNA molecule consisting essentially of a Sindbis virus RNA sequence which provides for the formation of Sindbis virus subgenomic messenger RNA (mRNA) molecules in transformed host cells.

BACKGROUND ART

Sindbis virus is a species of the Alphavirus genus which includes such important pathogens as Venezuelan, Western and Eastern equine encephalitis viruses. In nature, Sindbis virus is transmitted by mosquitos and its alternate vertebrate host is usually a bird or a mammal. In vitro, Sindbis virus infects a variety of avian, mammalian, reptilian, and amphibian cells. It also infects many species of mosquitos, a tick, and *Drosophila melanogaster*. Infection of vertebrate cells in culture is usually characterized by a dramatic cytopathic effect and rapid cell death, whereas growth in mosquito cells often leads to the establishment of chronic or presistent infections.

Figure 2:
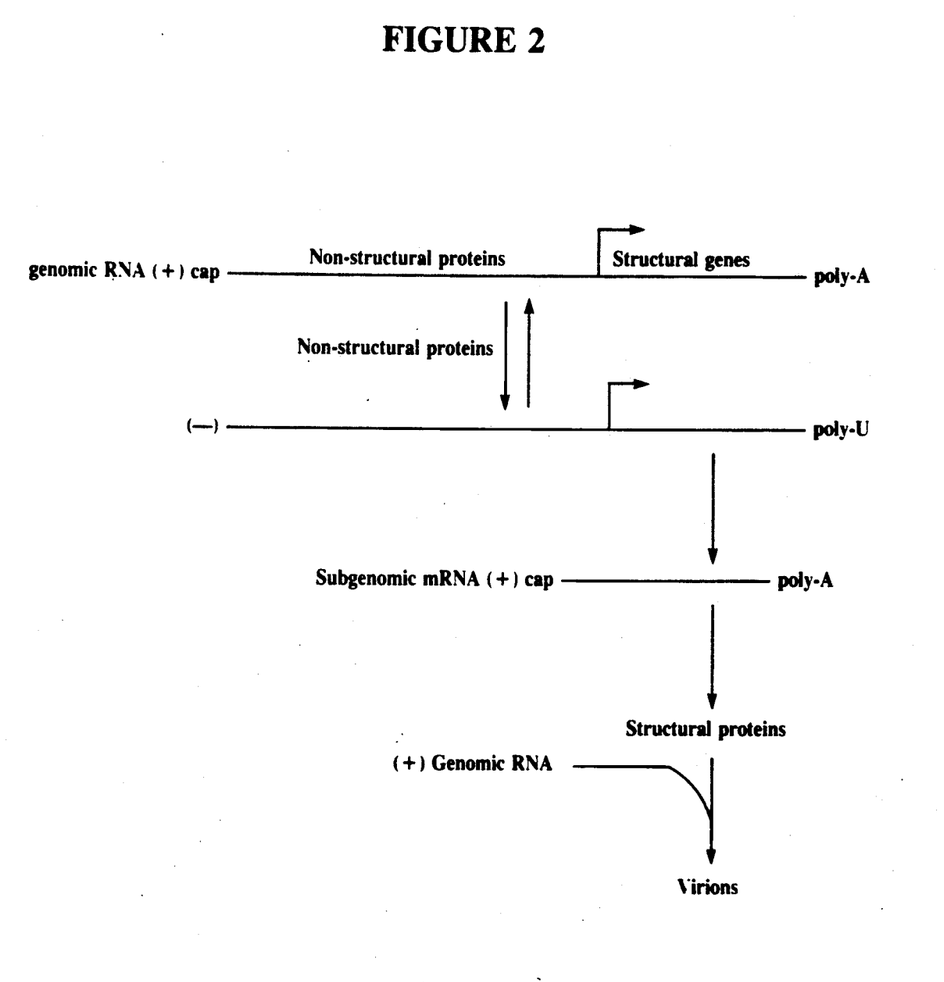
FIG. 2 depicts the life cycle of Sindbis virus.

Since its isolation in 1952, Sindbis virus and the closely related Semliki Forest virus have been widely studied (Schlesinger, S., and Schlesinger, M. J., 1986). The genome of Sindbis virus consists of a single molecule of single-stranded RNA, 11,703 nucleotides (nt) in length (Strauss, E. G. et al., 1984; Strauss, E. G. and Strauss, J. H., 1986). The life cycle of Sindbis virus is shown in FIG. 2. The genomic RNA is infectious, is capped at the 5' terminus and polyadenylated at the 3' terminus, and serves as mRNA and is therefore, by convention, of plus (+) polarity. The 5' two-thirds of the genomic 49S RNA is translated during early infection to produce two polyproteins that are processed by co-translational or post-translational cleavage into four nonstructural proteins (called nsP1 through nsP4, numbered in order as they appear in the genome sequence; Strauss, E. G. et al., 1984) presumably required for RNA replication. A full-length minus strand complementary to the genomic RNA is then synthesized. This minus strand then serves as a template for the synthesis of new 49S genomic RNA molecules and as a template for transcription of a 26S subgenomic mRNA molecule. Transcription of the minus strand begins at an internal site to produce the 26S subgenomic mRNA that is 4,106 nt long and colinear with the 3' terminal one-third of the 49S genome. The subgenomic mRNA is capped and polyadenylated. It does not serve as a template for minus strand synthesis, nor is it packaged into mature virions. Translation of the 26S mRNA produces a polyprotein that is cleaved co- and post-translationally by a combination of viral and presumably host-encoded proteases to give the three virus structural proteins, a capsid protein (C) and the two envelope glycoproteins (El and PE2, the precursors of the virion E2). The capsid protein complexes with the genomic RNA to form intracellular icosahedral nucleocapsids. These nucleocapsids interact with the cytoplasmic domains of the transmembrane envelope proteins, resulting in the budding of virus at the plasma membrane.

Three features of Sindbis virus suggest that it would be a useful vector for the expression of heterologous (e.g. foreign) coding sequences. First, is the previously discussed wide host range of Sindbis virus, both in nature and in the laboratory. Second, Sindbis virus gene expression occurs in the cytoplasm of the host cell and is rapid and efficient. During the 8-12 hours of a typical infection at 37° C., some $10^7$ to $10^8$ molecules of viral structural proteins are synthesized by each infected cell. Third, temperature-sensitive mutations in RNA synthesis are available that may be used to modulate the expression of heterologous coding sequences by simply shifting cultures to the non-permissive temperature at various time after infection.

Although the complete genomic sequence of Sindbis virus is known (Strauss, E. G. et al., 1984) and the coding regions for the viral proteins have been identified, the cis-acting sequences required for replication and transcription of infectious RNA molecules have heretofor not been identified. Utilization of Sindbis virus as an expression vector requires a determination of those virus sequences which allow for replication, transcription, and, ideally, packaging of the virus RNA before a heterologous coding sequence can be inserted into the virus RNA molecule.

Studies aimed at identifying conserved sequences among the alphavirus group have led to speculations as to the possible role of such conserved sequences in virus replication and transcription (see for review Strauss, E. G. and Strauss, J. H., 1986, and Ou, J-H. et al., 1982). No studies have yet been conducted, however, demonstrating the functionality of these conserved sequences in infectious RNA molecules. Furthermore, no suggestion has been made as to how or even if these conserved sequences can be employed to construct recombinant Sindbis virus vectors useful in expressing heterologous coding sequences. It remains to be determined how such virus sequences can be operably joined to heterologous coding sequences to provide for the replication, expression and/or packaging of heterologous coding sequences in infected host cells.

It is therefore an object of the present invention to identify the site(s) within the Sindbis virus genome where a heterologous coding sequence can be inserted without disrupting the ability of the recombinant molecules thereby created to be replicated and transcribed and, ideally, packaged by host cells containing such a recombinant molecule(s).

It is a further object of the present invention to construct Sindbis virus molecules (e.g., vectors) that contain at least one heterologous coding sequence, which molecules can provide for the replication and transcription (e.g., expression) of the heterologous coding sequence(s) in infected cells.

SUMMARY OF THE INVENTION

This invention encompasses novel compositions and methods which provide for the replication and expression of heterologous coding sequences in eucaryotic cells. In one aspect, the compositions of the present invention include nucleic acid molecules comprising at least one Sindbis virus junction region able to direct Sindbis virus subgenomic messenger RNA (mRNA) synthesis in a host cell. In one embodiment, the Sindbis virus junction region consists essentially of the following sequence, reading from the 5' end to 3' end:

AUCUCUACGGUGGUCCUAAAU AGU.

In another embodiment, the Sindbis virus junction region consists essentially of the following sequence, reading from the 5' end to the 3' end:

AUUACACCUGUCCUACU
GGCAUUGAGAACUUUUG
CCCAGAGCAAAAGAGCA
UUCCAAGCCAUCAGAGG
GGAAAUAAAGCAUCUCU
ACGGUGGUCCUAAAUAGU.

In another aspect, the compositions of the present invention include infectious Sindbis virus RNA molecules able to replicate, transcribe and express heterologous coding sequences in transformed host cells. In yet another aspect, infectious Sindbis virus particles comprising infectious Sindbis virus RNA molecules containing at least one heterologous coding sequence are provided.

In a further aspect, the present invention provides methods for both producing and utilizing the above compositions.

The compositions and methods of the present invention are particularly useful in providing a means for producing pharmacological, medical, agricultural and industrial compositions in a wide range of host cells by genetic engineering technology.

BRIEF DESCRIPTION OF THE DRAWINGS

In the following diagramatic representations, the nucleic acid sequences and/or molecules are provided in a left to right 5' to 3' orientation unless otherwise noted. The nucleotide regions marked as described below are for purposes of diagramatic representation and are not drawn to scale unless otherwise noted. The numbering and positioning of the Sindbis virus genomic nucleotides are according to Strauss, E. G. et al. (1984). The nucleotides adenine, guanine, cytosine, thymine and uracil are denoted A, G, C, T and U, respectively. The words "nucleotide(s)" and "kilobase(s)" are abbreviated "nt" and "kb", respectively.

FIG. 1 depicts the structure of full-length cDNA clones of Sindbis virus. The open arrow denotes the SP6 DNA-dependent RNA polymerase promoter. Extraneous sequences preceding the Sindbis virus sequences are indicated. The first and last four nucleotides of the Sindbis virus genome are shown. All clones have a 3' poly(A) tract ca. 35 nt long. The sequence between the poly(A) tract and the SstI site used for runoff transcription is shown. All clones consist of HRsp cDNA except the HR-derived sequences in Toto10 and Toto1000, indicated by filled-in bars extending from the ClaI site at nt 2713 to the BssHII site at nt 9804. Toto1000 contains an additional substitution from BssHII (nt 9804) to SstII (nt 11484) of HRsp cDNA, denoted by the stippled bar. The filled-in bar in Toto50 indicates HRsp-derived sequences, from ClaI (nt 2713 to SpeI (nt 5262), from an independent HRsp cDNA clone. The coding regions of the viral proteins are outlined at the bottom of the figure (nucleotide positions are indicated in kilobases). The plasmid beta-lactamase gene and replicon are not shown.

DETAILED DESCRIPTION OF THE INVENTION

The present invention relates to infectious Sindbis virus vectors, methods for their utilization in the expression of heterologous coding sequences in host cells and methods and compositions for creating the vectors of the present invention.

In the context of this disclosure, the following terms shall be defined as follows unless otherwise stated:

"heterologous coding sequence" means a nucleic acid (RNA or DNA) sequence, which is not naturally found in association with the nucleic acid sequences of the specified molecule. Typically, a heterologous coding sequence encodes a non-viral RNA sequence, molecule or protein. However, the term "heterologous coding sequence" can also include Sindbis virus sequences which have been altered by human manipulation to cause changes (e.g. nucleic acid deletions, substitutions, and/or additions) in the primary nucleic acid sequence and/or positioning in the native (e.g. naturally occurring) virus molecule;

"heterologous protein or peptide" means a protein, peptide and/or amino acid sequence not naturally encoded in a Sindbis virus genome;

"infectious", when used to describe a RNA molecule, means an RNA molecule which is self-replicating and provides for transcription in a host cell;

"replication" of the Sindbis virus genomic RNA and recombinant Sindbis virus RNA molecules means production of full-length equivalents of plus polarity using a minus strand RNA molecule as a template;

"transcription" of a Sindbis virus RNA molecule or recombinant molecule means production of a less than full-length plus polarity RNA molecule using a minus strand RNA molecule as a template;

"Sindbis virus junction region" is a Sindbis virus RNA sequence able to direct the transcription of an RNA molecule to produce a subgenomic messenger RNA (mRNA) molecule in a host cell;

"transfection" is understood to include any means, such as, but not limited to, adsorption, microinjection, electroporation, lipofection and the like for introducing an exogenous nucleic acid molecule into a host cell;

"transfected" or "transformed" when used to describe a cell means a cell containing an exogenously introduced nucleic acid molecule and/or a cell whose genetic composition has been altered by the introduction of an exogenous nucleic acid molecule.

The present invention relates to the discovery that heterologous coding sequences can be inserted into the structural region of the Sindbis virus genome without disrupting the ability of the recombinant molecules thereby created to retain their infectious nature. More specifically, the present invention relates to the discovery of the Sindbis virus cis-acting sequences which provide for the replication and transcription of Sindbis virus RNA, and/or heterologous coding sequences contained therein, in a host cell.

As it is technically difficult to engineer RNA molecules by current genetic engineering technology, manipulations of the Sindbis virus genome are best conducted in a DNA form. Thus, as described more fully in the examples herein, cDNA clones of the Sindbis virus genome, which cDNA clones encode infectious Sindbis RNA molecules are constructed. cDNA synthesis and cloning of Sindbis virus RNA from purified virus can be conducted by conventional recombinant DNA techniques. While the examples hereinafter describe the use of specific strains of Sindbis virus, it is understood that any other currently existing or future isolated strains of Sindbis virus, either natural or those created by human manipulation, can be utilized for this purpose. The creation of a cDNA clone encoding an infectious Sindbis virus RNA molecule can be confirmed either by DNA sequence analysis (confirmation that the cDNA sequence is a true copy of the Sindbis virus RNA template employed) or by subsequent transcription of the cDNA clone and assaying of the RNA molecules so produced for infectivity in a selected host cell in accordance with the methods described more fully hereinafter.

Briefly, transcription of Sindbis virus cDNA is achieved by inserting the cDNA sequence into a plasmid containing a DNA-dependent RNA polymerase promoter (RNA polymerase promoter) such that transcription of the Sindbis virus cDNA is under the control of said promoter. Examples of such promoters include, but are not limited to, the SP6 promoter (Rice et al., 1987), the bacteriophaze T7 promoter (van der Werf et al., 1986), an *E. coli promoter (Dawson et al., 1986 and Ahlquist et al., 1984)* and the bacteriophaze T3 promoter (Bailey et al., 1983 and Morris et al., 1986). RNA transcripts are then synthesized in vitro employing the RNA polymerase which recognizes the promoter selected. It was discovered that RNA transcripts of Sindbis virus cDNA preferably contain no more than about one to three nucleotides 5' to the natural start of the Sindbis virus genomic RNA, and preferably not more than one 5' nucleotide. Furthermore, it was discovered that for efficiency of transfection and optimization of production of infectious Sindbis virus RNA transcripts, run-off transcription of the cDNA clones should end within about 1 to about 100 nucleotides of the viral poly-A sequence with a most preferred transcriptional run-off site within about 1 to about 10 nucleotides downstream from the viral poly-A sequence.

Once a cDNA clone encoding infectious Sindbis virus RNA molecules is created, the clone can be manipulated to insert a desired heterologous coding sequence into the Sindbis virus cDNA. While the heterologous coding sequence typically encodes such pharmaceutically or therapeutically important proteins or peptides as hormones,( e.g. growth hormone, insulin, reproductive hormones and the like), enzymes (e.g. tissue plasminogen activator), immunologic growth factors, antibodies and/or other molecules and neurologic factors (e.g. nerve growth factor), the heterologous coding sequence can also encode intermediates and/or fragments of such proteins. Additionally, the heterologous coding sequence can encode such RNA molecules as viroids, transfer RNA's, ribozymes and/or anti-sense RNA. The size and number of heterologous coding sequences which can be inserted into infectious Sindbis virus RNA molecules is limited only if it is desired that the recombinant Sindbis virus molecules be packaged in infectious Sindbis virus particles. Indeed, as demonstrated hereinafter, infectious recombinant Sindbis virus molecules (e.g. vectors) can contain heterologous coding sequences encoding a single peptide of at least about 170 kilodaltons (Kd) or multiple peptides which cumulatively equal about 170 Kd and still be efficiently packaged into infectious Sindbis virus particles. Specifically, it is demonstrated, in the examples hereinafter, that recombinant Sindbis virus RNA molecules representing a size of about 106% of the natural viral RNA can be packaged in infectious Sindbis virus particles.

Efficient utilization of recombinant Sindbis virus RNA molecules for the expression of desired heterologous coding sequences minimally requires that the transfecting recombinant molecule can replicate itself (e.g. produce a minus strand from which replicates of the transfecting recombinant molecules are made) in the transfected host cell, thereby amplifying the number of heterologous coding sequences present in the transfected (infected) cell. Also minimally required is that the transfecting recombinant molecule can be transcribed (e.g. produce subgenomic RNA from the minus strand copy of the transfecting RNA molecule) in the transfected host cell. Expression of a heterologous coding sequence is understood to occur once transcripts comprising the heterologous coding sequence are made. These transcripts can then be further expressed as proteins, if so desired, by translation of the transcripts in the transfected cells.

Although the sequence of events involved in Sindbis virus replication are fairly well understood, a precise characterization of the factors and sequences involved in virus replication are not well characterized. To date, virus replication is believed to involve various trans-acting factors, such as a viral replicase, which are synthesized once the virus enters and is uncoated in an infected cell. These trans-acting factors then interact with or recognize specific sequences, commonly referred to as cis-acting sequences, on the genomic 49S RNA to generate a minus strand RNA molecule complementary to the genomic RNA. At least some trans-acting factors are believed to be encoded in the 5' two-thirds of the genomic 49S RNA. As demonstrated hereinafter, infectious recombinant Sindbis virus RNA molecules contain essentially all of the 5' 2/3 of the genomic RNA or functionally equivalent sequences thereof.

The cis-acting sequences have heretofor not been fully identified in infectious RNA molecules. From studies with Sindbis virus defective interferring (DI) RNA molecules, it has been determined that the first about 19 nucleotides immediately adjacent to and upstream from the viral poly A sequence are required for replication and packaging of Sindbis virus RNA into infectious virus particles. Thus, infectious recombinant Sindbis virus molecules should contain at least the first about 19 nucleotides immediately adjacent to and upstream from the viral poly A sequence, and preferably at least the first about 19 to about 62 nucleotides immediately adjacent to and upstream from the viral poly A sequence.

Similarly, the trans-acting factors and cis-acting sequences involved in the transcription of minus strand RNA into subgenomic Sindbis virus mRNA have heretofor not been characterized. It was known, prior to this invention, that the 26S subgenomic mRNA molecules begin at around nucleotide (nt) 7598 and that the coding region of the first virus structural protein, the capsid protein, commences about 49 nucleotides downstream from the 5'-end (nt 7598) or start of the subgenomic mRNA.

In light of the foregoing, it is a surprising result that, as demonstrated herein, heterologous coding sequences inserted into the structural region can be replicated and transcribed and furthermore translated at levels similar to that of the viral structural proteins in infected cells.

These heterologous sequences can be expressed as either a fusion protein, comprising part of the capsid protein and complete heterologous protein sequences, or as an intact heterologous protein. When expressed as an intact protein, the heterologous coding sequence must be preceded by a translation start signal codon (e.g. AUG). Packaging of recombinant Sindbis virus molecules in which the structural proteins are interrupted can be achieved by co-infecting transfected host cells with a helper Sindbis virus (e.g. virus expressing a functional structural protein or proteins).

Sindbis virus DI cDNA clones, which may or may not contain heterologous coding sequences downstream from the sequence being tested are then subjected to site-specific mutation and/or deletion analysis and subsequent screening for production of subgenomic RNA transcripts. By these means, it was discovered that the Sindbis virus junction region consists essentially of a region or sequence of nucleotides from about nt 7579 to about nt 7603, otherwise determined as being within at least the first about 19 nucleotides immediately upstream from the start of the Sindbis virus subgenomic mRNA and at least the first about 5 nucleotides immediately downstream from the start of the Sindbis virus subgenomic mRNA. The Sindbis virus junction region therefore consists essentially of the following sequence, reading from the 5' end to 3' end:

AUCUCUACGGUGGUCCUAAAU
    AGU.

The above sequence is given in a plus polarity even though it is recognized that the functional sequence is the complement thereof contained within the viral minus strand. Unless otherwise stated, junction sequences, positioning and nucleotide numbering are given in the plus polarity.

As demonstrated more fully in the examples herein, Sindbis virus sequences, both upstream and downstream from the herein identified Sindbis virus junction region can be retained in infectious recombinant Sindbis virus molecules without adversely affecting the ability of these molecules to be replicated and transcribed in infected host cells. Indeed, Sindbis virus junction regions comprising the following nucleotide sequence, reading from the 5' end to 3' end, are successfully employed to achieve transcription in transfected cells:

AUUACACCUGUCCUACU
    GGCAUUGAGAACUUUUG
    CCCAGAGCAAAAGAGCA
    UUCCAAGCCAUCAGAGG
    GGAAAUAAAGCAUCUCU

-continued
    ACGGUGGUCCUAAAUAGU.

As with the shortened Sindbis virus junction region sequence given previously above, it is understood that minimal changes in the nucleotide sequence can be made. Sequences containing such changes or alterations in nucleotide composition are considered to be equivalents of the sequences taught herein so long as the essential function (e.g. signaling of transcription) of these sequences is not diminished to an intolerable degree.

Sindbis virus junction regions of the present invention can be isolated as discrete fragments from infectious Sindbis virus cDNA clones or can be created synthetically by such conventional recombinant DNA techniques as restriction enzyme digestion or chemical DNA synthesis.

Inclusion of selected Sindbis virus sequences in addition to the Sindbis virus junction region in a Sindbis virus vector are predicated on the additional functionalities of the vector desired. For example, the viral sequences upstream from the Sindbis virus junction region and sequences within the first about 19 to about 62 nucleotides immediately adjacent to and upstream from the viral poly A sequence provide for replication of recombinant Sindbis virus molecules. Thus, these sequences should be included in an infectious recombinant Sindbis virus vector. Indeed, as demonstrated in the examples hereinafter, these sequences also contain the cis-acting signals for packaging in infectious virus particles.

The discovery and identification of the Sindbis virus junction region is highly significant as it now provides the means for employing Sindbis virus as a recombinant vector useful in the expression of heterologous coding sequences in a wide variety of host cells. Specifically, Sindbis virus vectors can be created by operatively joining a Sindbis virus junction region to the sequence that is desired to be expressed.

In one embodiment, operative joining can be achieved by creating or inserting a Sindbis virus junction region immediately upstream from the coding sequence to be expressed. In one preferred embodiment, the Sindbis virus junction region consisted essentially of the following sequence, reading from the 5' end to the 3' end:

AUUACACCUGUCCUACU
    GGCAUUGAGAACUUUUG
    CCCAGAGCAAAAGAGCA
    UUCCAAGCCAUCAGAGG
    ACGGUGGUCCUAAAUAG
    UCAGCAUAGU, and immediately preceding the AUG of the coding sequence desired to be expressed.

As demonstrated in the Examples, hereinafter, an infectious Sindbis virus vector can also be created by inserting a heterologous coding sequence or sequences into a Sindbis virus genome anywhere downstream from the first about 5 nucleotides of the start of the Sindbis virus subgenomic mRNA. Insertion of such heterologous coding sequences can be accomplished by employing already existing restriction endonuclease sites in the described structural region of infectious Sindbis virus cDNA clones or by employing an artificially introduced restriction endonuclease site or sites in the structural region. As demonstrated herein, such heterologous coding sequences can encode a protein or proteins which is, individually or collectively, are at least about 170 kd in size and can be subsequently expressed as intact RNA molecules, fusion proteins or intact proteins in cells transfected with RNA transcripts made from such clones.

Additionally, it is believed that expression and subsequent secretion of a desired heterologous protein can be achieved by operatively joining a Sindbis virus junction region to a gene comprising a signal sequence and a DNA sequence encoding the protein to be secreted. In one embodiment, an infectious Sindbis virus vector able to direct the secretion of a desired protein is created by inserting a coding sequence downstream from a Sindbis virus envelope protein signal sequence. In another embodiment, a heterologous coding sequence operatively joined to a eucaryotic signal sequence can be inserted into the structural region of an infectious Sindbis virus vector such that secretion of the heterologous protein is controlled by the eucaryotic signal sequence and transcription is controlled by a Sindbis virus junction region.

Thus, the operative joining of a Sindbis virus junction region to a heterologous or desired coding sequence includes the insertion of a coding sequence(s) within a virus structural gene sequence, the transcription of which is naturally controlled by a Sindbis virus junction region.

Furthermore, the discovery and identification of the Sindbis virus junction region provides a means for facilitating the expression of multiple heterologous coding sequences in a wide variety of host cells and for constructing infectious and self-packing recombinant Sindbis virus molecules. Indeed, as demonstrated in the Examples hereinafter, just such an infectious and self-packaging recombinant Sindbis virus molecule can be generated. Briefly, a heterologous DNA molecule is prepared which contains, in order from it's 5' to 3' end, a Sindbis virus junction region and a DNA sequence encoding a desired heterologous protein which is no more than about 25 Kd in size. The heterologous DNA molecule is then inserted into an infectious Sindbis virus clone downstream from the structural coding region and upstream from the first about 19 nucleotides immediately adjacent to and upstream from the viral poly A sequence to create a recombinant Sindbis virus clone.

Alternatively, a recombinant Sindbis virus clone can be constructed by inserting a desired heterologous coding sequence upstream from the structural coding region and immediately downstream from the first about 5 nucleotides of the Sindbis virus subgenomic start site and by inserting a Sindbis virus junction region at a site preceding the capsid gene and downstream from the heterologous coding sequence. RNA transcripts made from such recombinant Sindbis virus clones can then be employed to transfect a desired host cell thereby providing for the replication, expression and self-packaging of recombinant Sindbis virus molecules in infectious virus particles.

Thus, the operative joining of a Sindbis virus junction region to a heterologous coding sequence further includes the placement of the heterologous coding sequence downstream from a Sindbis virus junction region so that the production of subgenomic mRNA molecules comprising the heterologous coding sequence are under the control of the Sindbis virus junction region.

As previously stated, a wide range of host cells can be employed in the methods of the present invention. Examples of such host cells include insect, avian, mammalian, reptilian and amphibian cells, further detailed in the Examples hereinafter.

Materials and Methods

Sindbis virus stocks derived from Sindbis virus cDNA clones described herein as well as the HR small plaque strain (HRsp, stock no. 80-5724) described by Strauss, E. G. et al. (1984) and an HR large plaque strain (HR) described by Burge and Pfefferkorn (1966a and 1966b) are grown on monolayers of primary or secondary chicken embryo fibroblasts (CEF) and titers are determined in accordance with the methods described by Strauss, E. G. et al. (1976). The virus is purified by centrifugation, clarification of the culture media followed by polyethylene glycol precipitation from the culture media, followed by successive velocity sedimentation and equilibrium density centrifugations as described by Pierce, J. S. et al. (1974). The isolation of intracellular and virion RNA is as described by Rice, C. M. et al. (1987).

Restriction endonucleases and DNA modifying enzymes are purchased from commercial sources and used in accordance with manufacturers' instructions. Bacterial plasmids are grown, purified and analyzed by standard methods as essentially described by Maniatis, T. et al. (1982).

cDNA synthesis and cloning of Sindbis virion RNA from purified virus is conducted as described by Rice, C. M. and Strauss, J. H. (1981) and Strauss, E. G. et al. (1984).

Double-stranded cDNA restriction fragments used to construct derivatives of Toto5 ar purified by extraction from preparative low-melting-temperature agarose gels as described by Weislander, L. (1979).

For sequence analysis of RNA prepared from Toto1000- and Toto1002-infected CEF cells, a 5'-end-labeled oligonucleotide [complementary to nucleotide (nt) 7644 through nt 7662 of the Sindbis virus genome; Strauss, E. G. et al. (1984)] is annealed to total cytoplasmic RNA and extended with avian myeloblastosis virus reverse transcriptase. Discrete extension products corresponding to the 5' end of 26S RNA are isolated from a preparative sequencing gel and sequenced by the chemical method described by Maxam and Gilbert (1980).

The transcription of Sindbis virus clones containing Sindbis virus cDNA with or without heterologous coding sequences is as follows. RNA transcripts are synthesized in vitro by SP6 RNA polymerase with either supercoiled plasmid templates or plasmid DNA's digested with appropriate restriction endonucleases for production of runoff transcripts. Reactions containing 40 mM Tris chloride (pH 7.6); 6 mM $MgCl_2$; 2 mM spermidine; 1000 units/ml RNase inhibitor (Promega; Madison, Wis); 100 µg/ml bovine serum albumin (BSA) (Pharmacia; New Jersey); 1 mM each ATP, CTP, UTP, and GTP; 100 µg of template DNA per ml are incubated at 38° C. to 40° C. for about 1 hour (see Butler, E. T. and Chamberlain, M. J., 1982; Krieg, P. A. and Melton, D. A., 1984; and Melton, D. A. et al., 1984). 5'-capped transcripts are produced by inclusion of 1 mM $m^7G(5')ppp(5')G$ or $M^7G(5')ppp(5')A$ cap analogs in the transcription reaction (see Konarska, M. M. et al., 1984). Trace quantities of $^3H$-UTP or [$\alpha$-$^{32}P$]CTP included in the transcription reactions allow quantitation and gel analysis of the RNA transcripts. Incorporation is measured either by trichloracetic acid precipitation or by adsorption to DE 81 filter paper (Whatman, Inc., Clifton, N.J.) as described in Maniatis, T. et al. (1982).

The screening of transcripts made from Sindbis virus cDNA clones for the presence of infectious RNA is as follows. For rapid assay of transcript infectivity or for production of virus stocks, the transcription mix is used directly for transfection. For purified transcripts, the template DNA is removed by digestion with RNase-free DNase I, followed by extraction with phenol-chloroform and ethanol precipitation. Typically, confluent monolayers of secondary CEF in 35 mm tissue culture plates (about $10^6$ cells) are used for transfection. After washing once with Eagle minimal essential medium with Earle salts (MEM) without serum, the cells are incubated with 1.5 ml of MEM containing 50 mM Tris chloride (pH 7.3) (at 25° C.) and 200 µg of DEAE dextran per ml (average molecular weight, 500 kilodaltons [KD]; Sigma Chemical Co., St. Louis, Mo.) for 15 to 60 minutes at 37° C. This medium is removed and 200 µl of RNA or transcription mix (diluted in phosphate-buffered saline) is added to the cells and incubated at room temperature for 15 to 60 minutes with occasional rocking. Plaque forming units (PFU) are quantitated by overlaying the monolayers with 2 ml of 1.2% agarose (SeaKem; FMC Corp., Marine Colloids Div., Rockland, Me.) diluted 1:1(v/v) in MEM and 2% fetal calf serum followed by incubation at 37° C. for wild-type stocks or at 30° and 40° C. for ts mutants. Plaques are visualized by staining with neutral red or crystal violet after 24 to 48 hours (37° or 40° C. incubation) or 48 to 72 hours (30° C. incubation). For production of virus stocks, the transfection mix is removed after the initial adsorption period and the cells are incubated with 2 ml of MEM containing 2% fetal calf serum for 24 (37° C.) or 48 hours (30° C.).

Alternatively, monolayers of CEF are transformed by lipofection. Essentially, the procedure described by Felgner, P. L. et al. (1987) is adapted to RNA transfection. The efficiency of the procedure can be enhanced by high salt treatment of cells (Stollar et al., 1967).

Quantitation of the bacterial chloramphenicol acetyl transferase (CAT) protein in transfected host cells is determined as follows. Parallel plates of CEFs are transfected with the in vitro transcripts of Sindbis virus cDNA clones containing a CAT coding sequence and incubated 24 hours at 37° C. Cells from one set of plates are harvested to measure total CAT enzyme activity (see Shaw, W. V., 1975; Gorman et al., 1982) produced by transfected cells. The other set is incubated under identical conditions, and then processed to assay, by immunofluroescence labeling for CAT protein, the number of transfected cells. Specifically, cells are fixed with 4% (w/v) freshly prepared paraformaldehyde in phosphate buffered saline (PBS) for one hour at 4° C. The monolayers are then washed and excess paraformaldehyde neutralized with 1 mg/ml glycine for 10 minutes. Cells are permeabilized with 0.5% (v/v) Triton X-100 in PBS and nonspecific protein binding is blocked using 2% (w/v) bovine serum albumin and 2% (v/v) horse serum. Cells are then incubated for one hour at room temperature with a 1:500 dilution of affinity purified rabbit anti-CAT antibody from 5 Prime-3 Prime, Inc. (West Chester, Pa.) that has been pre-adsorbed with methanolfixed CEFs. After washing three times at room temperature, with PBS plus 0.1% bovine serum albumin, the cells are treated with a 1:100 dilution of a fluorescein-labelled goat anti-rabbit IgG antibody (Boehringer Mannheim Biochemicals, Indianapolis, Ind.).

Production of tissue plasminogen activator (tPA) by cells transfected with Sindbis virus vectors containing tPA coding sequences is determined as follows. Media from transfected cells is harvested 20 hours post-transfection and assayed using the fibrin plate method described by Granelli-Piperno and Reich (1978) using tPA (at least 50,000 IU/mg) purchased from Sigma Chemical Co. (St. Louis, Mo.) as a standard.

The relevant portions of the references cited in both the Materials and Methods and Examples are hereby incorporated by reference herein.

EXAMPLE 1

Construction of Intermediate Sindbis cDNA Clones

This example demonstrates the construction of DNA molecules which contain full length cDNAs of the Sindbis virus genome positioned such that transcription of the Sindbis virus cDNA is under the control of a DNA-dependent RNA polymerase promoter, exemplified herein by the bacteriophage SP6 promoter (Melton, D. A. et al., 1984).

a. Construction of Toto1

A full-length cDNA clone of Sindbis virus HRsp, desiqnated Toto1 (FIG. 1), is oonstructed from four HindIII subclones of the Sindbis virus genome used for determination of the Sindbis virus sequence described by Strauss, E. G. et al. (1984). The HindIII cDNA fragments are then subcloned into a Proteus 1 plasmid. Proteus 1 consists of the replicon and the beta-lactamase gene of pBR322, from the ThaI (position 2522) to EcoRI (position 1) sites, with the ThaI end fused to the filled-in BglII-ClaI fragment from SP6 phage containing a SP6 DNA-dependent RNA polymerase promoter (see Melton et al., 1984). A polylinker sequence (5'-AAGCTTCTAGAGATCTGCAGGTCGACG-GATCCCCGGGAATTCCGCGGAATT-3') is positioned between the ClaI site from SP6 phage and the filled-in EcoRI site from pBR322.

The 5' terminus of Sindbis virus cDNA is fused to the SmaI site in the polylinker of Proteus1. The GC tail at the 5' terminus regenerates the SmaI site. The SmaI site is then converted to a ClaI site by cutting with SmaI and ligating in ClaI linkers (pCATCGATG), and it is used to fuse the Sindbis virus 5' terminus to the ClaI site downstream of the SP6 promoter. This 5' clone includes the HindIII site at position 125 of Sindbis virus. The 3' terminus of Sindbis virus cDNA is cloned as a HindIII (position 6267) to the poly(A)-poly(T) fragment between the HindIII and SmaI sites of Proteus1. The 5' and 3' clones are combined by ligating at the respective HindIII sites. (The SstII site in the polylinker is converted to a SstI site by using Sstl linkers, for subsequent runoff transcription). The two internal HindIII fragments (nt 125 to 1302 and 1302 to 6267) are then inserted, in the correct order and orientation, in the HindIII site of the 5'-3' clone to produce Toto1. Toto1 has 198 nt between the SP6 transcription start and the 5' nucleotide of the Sindbis virus gemone, including 9G residues derived during cDNA cloning, immediately 5' to the Sindbis virus sequences. The 3'-terminal poly(A) tract consists of ca. 35 residues followed by the sequence 5'-GGGAATTCGAGCTC-3', the last six nucleotides of which comprise the SstI site used for runoff transcription.

b. Construction of Toto5

Toto1 is modified by inserting a ClaI linker (pCATCGATG) into the HaeIII site in SP6-derived sequences, cutting with ClaI and ligating to the SP6-derived ClaI downstream of the SP6 promoter (see above). This modification leaves 48 nucleotides (nt) between the SP6 transcription start and the Sindbis virus cDNA 5' nucleotide. All SP6-derived sequences preceding the Sindbis virus sequences are then deleted. Specifically, taking advantage of an HphI recognition sequence in the SP6 promoter, which sequence directs HphI cutting after the A one nt 3' from the G that corresponds to the major transcriptional initiation site for SP6 DNA dependent RNA polymerase (Kang, C. and Wu, C-W., 1987), the HphI cut site, previously treated with T4 DNA polymerase to remove the 3' protruding A, is fused to a SfaNI site (filled in by treatment with the large fragment of DNA polymerase I) created by the HaeIII-ClaI linker fusion described above. The resultant DNA clone, designated Toto3 (FIG. 1), has eight extra G's preceding the Sindbis virus sequences.

Figure 1:
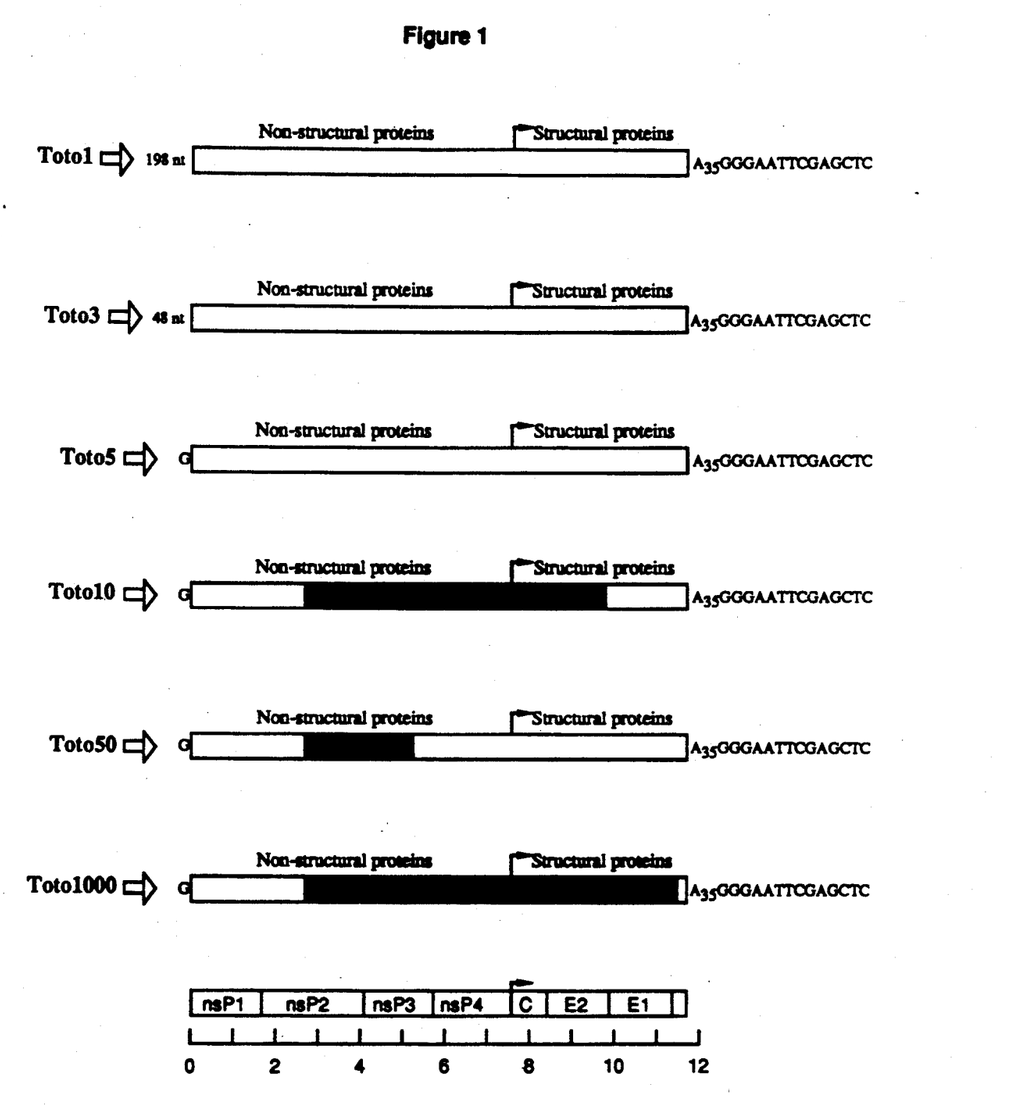

Toto5 is created from Toto3 by removing all but one extra G. Specifically, the fragment from Toto3 containing the SP6 promoter and the 5'-terminal 125 nt of Sindbis virus (to a HindIII site at position 125) is subcloned into a plasmid designated πAN8 (Hollifield et al., 1987). This clone, called πK1, has a unique RsaI site 14 nt downstream from the Sindbis virus 5' terminus and a unique HphI recognition site in the SP6 promoter (see above). A pair of complementary synthetic oligonucleotides, corresponding to the Sindbis virus 5' terminus through nt 14, is ligated to RsaI- and HphI-digested and T4 DNA polymerase-treated πK1. The resulting clone, πK2, is verified by sequence analysis, and the SP6 promoterSindbis virus 5'-terminal sequences are recloned into Toto3 to give Toto5 (FIG. 1). As demonstrated by Rice, C. M. et al (1987), the Toto5 clone does not produce infectious Sindbis virus transcripts as it contains two lethal point mutations.

EXAMPLE 2

Construction of Sindbis Virus cDNA Clones Encoding Infectious Sindbis Virus Transcripts This example demonstrates the construction of DNA molecules comprising cDNAs encoding infectious Sindbis virus transcripts and which cDNAs are under the transcriptional control of a DNA-dependent RNA polymerase promoter, exemplified herein by the bacteriophage SP6 promoter.

As shown in FIG. 1, Toto10, Toto50 and Toto1000 are created from Toto5 as follows. The ClaI (nt 2713 of the Sindbis virus cDNA) to BssHII (nt 9804 of the Sindbis virus cDNA) interval of Toto5 is replaced with the corresponding Sindbis virus HR cDNA to create Toto10 (FIG. 1). In order to create Toto1000, the BssHI (nt 9804) to SstII (nt 11484) interval of Toto10 is replaced with the corresponding Sindbis virus HRsp cDNA. Toto10 and Toto1000 are therefore hybrids of Sindbis virus HRsp and HR (FIG. 1). Toto50, also a derivative of Toto5, is created by substituting the ClaI (nt 2713) to SpeI (nt 5262) region of Toto5 with that from an independent subclone (of the HindIII [nt 1302] to HindIII [nt 6267]region) of cDNA from Sindbis virus HRsp (FIG. 1).

Toto1101 is derived from Toto1000 by replacing the 3'site used for runoff transcription with a XhoI site. λToto1101, a lambda phage clone of a full-length copy of the Sindbis virus genome downstream from the SP6 promoter, is constructed from λgtWES-λB described by Leder, P. D. et al. (1977), by replacing the SstI to XhoI region (λ positions 25881 to 33498) with the SstI to XhoI fragment of Toto1101 containing the SP6 promoter and Sindbis virus genome.

Toto1002 is created as follows. A plasmid clone, designated πnsP4Cl, consisting of an AccI (nt 7492) to NcoI (nt 8038) region of Toto1000 cloned in πAN7 (Lutz et al., 1987), is digested with RsaI (nt 7611) and ligated in the presence of 43 mM XbaI linker (pTCTAGA). After transformation, clones that contain the XbaI linker are selected by digestion with XbaI, isolation of the linear DNA, ligation and retransformation. A representative clone, designated πClR, with a single XbaI linker inserted at RsaI (nt 7611) is then extended in the 5' direction by cloning into the HindIII (nt 6267) to AccI (nt 7492) interval from Toto1000. The resulting clone, designated πnsP4CR, contains unique HpaI (nt 6919) and AatII (nt 7999) sites which are then used to exise the XbaI linker containing fragment for replacement into Toto1000 to give Toto1002.

Screening of the Sindbis virus cDNA clones of this Example 2 for infectious Sindbis virus transcripts is as described in the Materials and Methods, above. Template DNA's did not need to be purified by banding on CsCl gradients, and several protocols for rapid plasmid and phage DNA preparation are satisfactory, provided that the template DNA is RNase-free and salt-free (see Butler, E. T. and Chamberlain, M. J., 1982). Transcripts made from supercoiled plasmid DNA from minipreps are infectious. However, their specific infectivities are variable, typically about 10-fold lower than the transcripts produced by runoff transcription. RNA products which comigrate with full-length runoff transcripts are found when either uncut lambda or supercoiled plasmid templates are used, and such products may result from the falloff of the SP6 polymerase in the poly(A) tract or shortly thereafter. By these methods, transcripts from Sindbis virus cDNA clones, Toto10, Toto50, Toto1000, Toto1002, Toto1101 and λToto1101 are found to be infectious.

EXAMPLE 3:

Construction of Sindbis Virus Clones Containing Heterologous Coding Sequences

Figure 3:
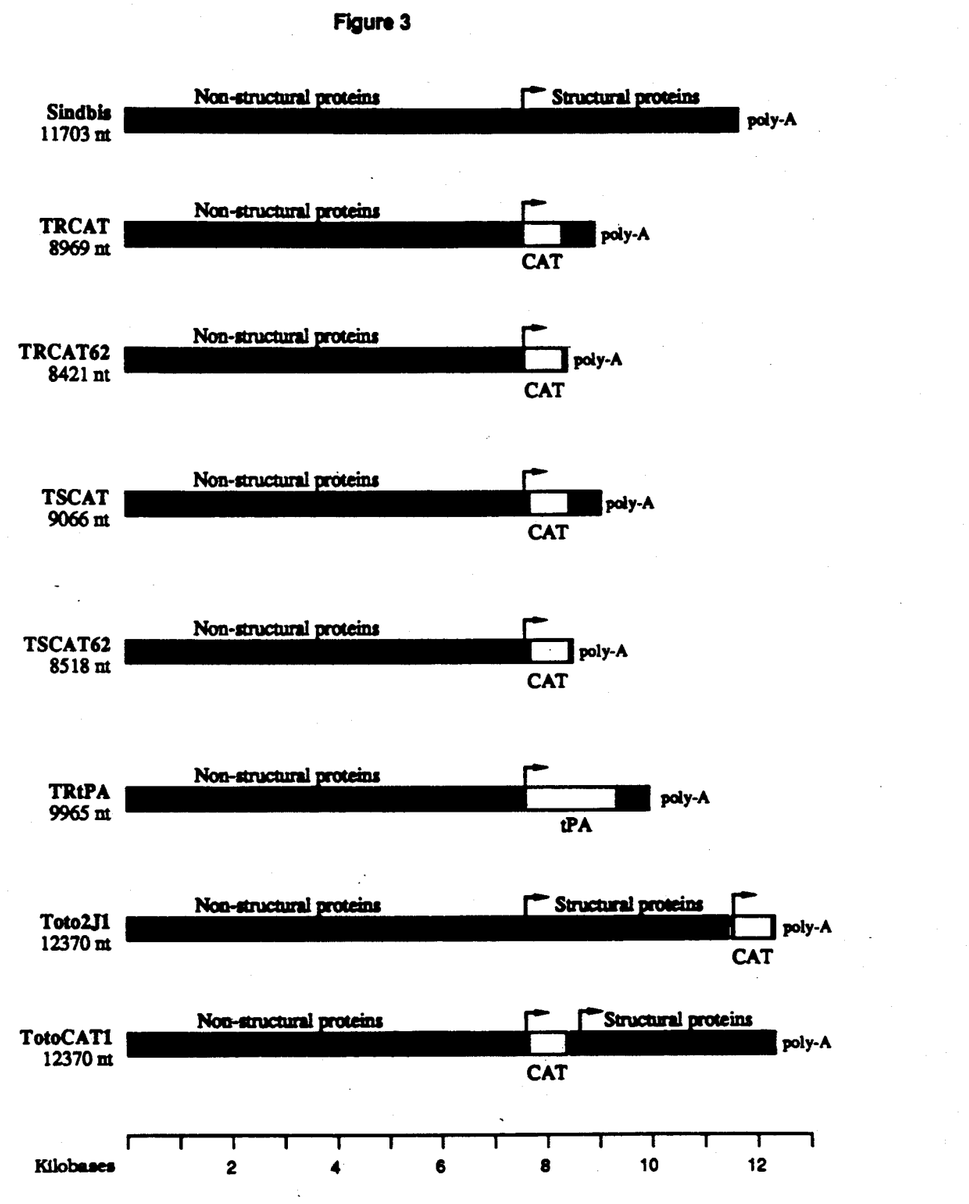
FIG. 3 depicts the structure of Sindbis virus, TRCAT, TRCAT62, TSCAT, TSCAT 62, TRtPA, Toto2J1 and ToToCAT1. The open bars indicate heterologous coding sequences. The directional arrow denotes the start and direction of the Sindbis virus subgenomic messenger RNA (mRNA). The size of the clones is indicated in kilobases outlined at the bottom of the figure.

This example demonstrates the construction of Sindbis virus clones able to give rise to self-replicating Sindbis virus vectors able to express heterologous coding sequences in cells transformed with said vectors. As shown in FIG. 3, construction of such Sindbis virus clones generally involves either the insertion of desired heterologous sequences within the structural coding region of the virus genome or the removal or deletion of all or a portion of the virus structural region sequences and the replacement of said sequences with desired heterologous coding sequences. In this Example 3, we demonstrate the construction of Sindbis virus clones which can give rise to Sindbis virus vectors able to express heterologous sequences as a fusion with structural virus proteins or sequences, or as intact (e.g. nonfusion) proteins or sequences.

a. Sindbis Virus Clones Containing CAT Coding Sequences

Eight distinct Sindbis virus clones containing DNA sequences coding for CAT (e.g. a CAT gene) are created.

One clone, designated TSCAT (FIG. 3), is created as follows. A DNA sequence coding for the CAT protein is isolated from the chloramphenicol resistance transposon Tn9 described by Alton, N.K. and Vapnek, D. (1979) as a TaqI fragment. The ends of the TaqI fragment are then modified by conventional methods to insert a XbaI site just 5' to the CAT coding sequence and a XhoI site just 3' to the CAT coding sequence. The so modified fragment, designated CATa, is then inserted into Toto1000 so as to replace the SstII (nt 7716) to SalI (nt 11087) region of Toto1000. The resultant plasmid, designated TSCAT thus retains 117nt downstream of the initiation site for the viral subgenomic mRNA and gives an in-frame fusion of 23 codons of the capsid protein, 17 codons of the polylinker and 5' untranslated sequences of the CAT gene, followed by the CAT coding sequences.

A derivative of TSCAT, designated TSCAT-ts-6, is also made that carries the ts-6 mutation described by Burge, B. W. and Pfefferkorn, E. R. (1966a) and Strauss, E. G. and Strauss, J. H. (1980). The ts-6 mutation is a glycine to glutamate change at residue 153 of Sindbis virus non-structural protein 4 (nsP4, FIG. 1). Virus with the ts-6 mutation grows well at 30° C., but not at 40° C. because RNA synthesis ceases shortly after shifting infected cultures to the non-permissive (40° C.) temperature.

A third, clone, designated TRCAT (FIG. 3), is created by inserting the CATa fragment, described above, into Toto1002 thus replacing the XbaI to SalI region of Toto1002. Toto1002 contains an XbaI (TCTAGA) linker in the RsaI site (nt 7611) of Toto1000 (Rice, C. M. et al., 1987). The resultant TRCAT clone retains only 14 nt downstream of the initiation site of the viral subgenomic mRNA such that the first translation initiation codon in the subgenomic mRNA is that of the CAT gene. Both TSCAT and TRCAT retain 616nt, plus the poly-A sequence, of the 3' end of the Sindbis virus genome.

A fourth clone, TRCAT62, is constructed as follows. An XhoI oligonucleotide (pCCTCGAGG) is inserted into the Fnu4HI site at nucleotide 11641. This is fused to the XhoI site in the polylinker 3' of the CATa module to give a CATa-3 '62 nucleotide poly-A module. An XbaI site in the polylinker 5' of the CATa module is used to fuse the module to the XbaI site of Toto1002 thereby replacing the Sindbis virus structural region with the CATa-3 '62 nucleotide poly-A module.

A fifth clone, designated TSCAT62 (FIG. 3), is created by replacing the CATa-Sindbis virus 3' region (from SalI at nt 11087 through the poly A sequences) with the CATa-3 ' 62 nucleotide poly A module used in the construction of TRCAT62 described above.

A sixth clone, designated Toto2J1 (FIG. 3), is created as follows. The SstI to NsiI (nt 11452) fragment from Toto1001, consisting of, in order, the SP6 RNA polymerase promoter, the entire Sindbis virus genome to NsiI (partial digest, T4 DNA polymerase treated), is ligated to the SspI (nt 7499, partial digest) to SstI fragment from TRCAT62. The latter fragment consists of, in order, 98 nucleotides upstream of the subgenomic start (nt 7598), 14 nucleotides of the 5' untranslated sequence of the subgenomic mRNA, polylinker and CAT sequences, 62 nucleotides of Sindbis 3' untranslated sequence, the Sindbis virus poly-A sequence.

A seventh clone, designated TotoCAT1, is created in two steps, as follows. The XbaI to XhoI segment of TRCAT62, consisting of the CATa-3 ' 62 nucleotide poly-A module was replaced with the XbaI to NsiI (11452, T4 DNA polymerase treated) fragment from Toto1002 (consisting of the entire structural protein coding sequences through NsiI 11452 in the Sindbis virus 3' untranslated region). This clone, Toto1003, gives infectious in vitro transcripts, and is equivalent to Toto1002 with a deletion of NsiI (nt 11452) to Fnu4HI (nt 11641) in its 3' untranslated region. To make TotoCAT1, the SspI (nt 7499, 98 nt 5' of the start of the subgenomic RNA start site) to MluI (runoff transcription site just 3' of the Sindbis virus poly-A sequence) fragment of Toto1003 was inserted into TRCAT62, replacing the XhoI (filled-in) to MluI (runoff transcription site just 3' of the Sindbis virus poly-A sequence) fragment, consisting of the 3 ' 62 nucleotide poly-A sequences, of TRCAT62.

The eighth clone, designated TLXNCAT, is derived from clone TLXN as described below.

b. Sindbis Virus Clone Containing tPA Coding Sequence

A HeLa cell derived cDNA coding for tPA is obtained from Dr. Edmund K. Waller (Rockfeller University, New York City, N.Y.). The DNA sequence obtained is as described by Waller, E. K. (1984) and contains the entire tPA gene (e.g. DNA sequences coding for the 5' non-translated region, the signal sequence, the pro-tPA sequence, the mature protein sequence and 3' non-translated region). The tPA cDNA is then inserted into an M13mp18 cloning vector as follows. The 5' portion of the cDNA is excised from the clone obtained and described by Waller, E. K. (1984) using the restriction endonuclease SacI (or SstI, an isoschizomer) which cuts in the 5' non-translated region of the tPA gene and at the DNA codons for tPA amino acid number 411 (wherein amino acid "1" is the first amino acid of the mature tPA protein). This isolated fragment is then cloned into M13mp18 at the SacI site. The 3' portion of the tPA cDNA is isolated from the clone obtained and described by Waller, E. K. (1984) as a SacI to BglII fragment and is cloned into a second M13mp18 cloning vector at the SacI and BglII site. The individual M13mp18 vectors containing the 5' or 3' portions of the tPA gene are then individually subjected to oligonucleotide-directed site-specific mutagenesis (Zoller, M. J. and Smith, M., 1983) to insert BamHI restriction sites just 5' and 3' to the tPA gene. Following mutagenesis, the 5' and 3' portions of the tPA gene are isolated and religated at their respective SacI sites and the reconstructed tPA gene then inserted into a M13mp18 cloning vector. The tPA gene is then isolated from the M13mp18 cloning vector as a KpnI to SalI fragment and inserted into the KpnI to SalI sites of Prot31Sin3-'SalI, that consists of the Sindbis 3' region from SalI (11087) through the poly-A sequence, cloned into a polylinker of an ampicillin resistance, pBR322-derived plasmid giving P31tPA3' The tPA-Sindbis 3' module is cut out with Asp718I (filled-in) and XhoI, inserted into and replacing the XbaI (filled-in) to XhoI region of Toto1102. Toto1102 is identical to Toto1002 except for an XhoI runoff instead of the SstI runoff just downstream of the Sindbis poly-A sequence.

c. Sindbis Virus Clones Containing a Polylinker

A Sindbis virus clone, designated TLXN, containing a polylinker is created as follows. First, an adapter plasmid, designated P3S, is constructed. P3S consists of a pBR322-derived amplicillin resistance plasmid with a SP6 RNA polymerase promoter upstream of a polylinker containing restriction sites for restriction enzymes KpnI, ClaI, HindIII, XbaI, BglII, PstI, SalI, BamHI, EcoRI, XhoI, NotI, StuI and MluI. The specific polylinker sequence is as follows: 5'- GGTAC-CATCG ATAAGCTTCT AGAGATCTGC AGGT-CGACGG ATCCCCGGGA ATTCCTCGAG CGGCCGCAGG CCTACGCGT - 3', where the first G of the KpnI site is the initiating nucleotide for the SP6 RNA polymerase promoter. The polylinker is upstream of the Sindbis 3' untranslated sequences from nt 11453 through the poly-A sequences. The transcriptional runoff site is a SstI site. the polylinker Sindbis 3' fusion consists of the MluI site (filled in) of the polylinker fused to the Sindbis NsiI site at nt 11452 (T4 DNA polymerase-treated) so that the MluI site is regenerated. Sindbis virus clone TLXN consists of Toto1002 with the XbaI to NsiI region replaced with the XbaI to MluI portion of the polylinker of plasmid P3S. Specifically, the XbaI to PvuI fragment of plasmid P3S (the PvuI site is in the plasmid), consisting of the polylinker-Sindbis 3' module, is ligated to the PvuI to XbaI fragment of Toto1002, comprising, in order, the SP6 RNA polymerase promoter, the Sindbis nonstructural region and up to and including 14 nucleotides of the 5' untranslated sequence of the Sindbis subgenomic mRNA.

The TLXN clone and plasmid P3S are useful intermediates in the creation of infectious Sindbis virus molecules which contain at least one heterologous coding sequence. Heterologous DNA coding sequences can, for example, be cloned directly into TLXN utilizing any one or more of the unique restriction endonuclease cleavage sites encoded in the polylinker contained in TLXN. Indeed, when the XbaI to XhoI CATa module is inserted into TLXN previously cleaved with XbaI and XhoI to create TLXNCAT, the TLXNCAT transcripts are positive for CAT expression when transfected into CEF's.

Similarly, a desired heterologous coding sequence can be cloned into the polylinker of plasmid P3S after which cloning, any 5' polylinker site remaining can be fused to the XbaI site, of e.g. Toto1002 so as to create a Sindbis virus clone encoding infectious recombinant Sindbis virus RNA able to replicate and express the heterologous coding sequence contained therein.

EXAMPLE 4

Replication and Expression of Heterologous Coding Sequences in Transformed Cells This example demonstrates the ability of the Sindbis virus vectors of the present invention to provide for both the replication and expression of heterologous coding sequences (e.g. CAT and tPA genes) in transformed cells. In this example, tPA is produced as an intact, mature protein and enzymatically active CAT protein is produced as either an intact protein or as a fusion protein comprising 5' terminal sequences of the viral capsid protein and the CAT protein.

Self-replicating Sindbis virus vectors containing a DNA sequence encoding the tPA or CAT protein are produced by transcribing Sindbis virus clones containing a tPA or CAT gene. Specifically, clones TRtPA, TRCAT, TRCAT62, TSCAT, TSCAT62, TSCAT-ts-6, Toto2J1 and TotoCAT1 are individually transcribed in vitro using SP6 DNA-dependent RNA polymerase as described in the Materials and Methods above. The RNA transcripts so produced are then transfected into one or more of the following cell lines: chicken embryo fibroblasts (CEF's) mosquito (Aedes albopictus C7-10), Drosophila (Schneider 1), quail (QT-6), hamster (BHK), Chinese hamster ovary (CHO), mouse (3T3), or human (SW13), using the DEAE-dextran or lipofection methods described above.

Transfected (e.g. transformed) cells (for CAT assay) or culture media (for tPA assay) are then harvested at various times (e.g. 0, 4, 8, 12, 16 or 20 hours) post-transfection and assayed for tPA or CAT production in accordance with the methods described above. The replication of the Sindbis virus RNA vectors containing heterologous coding sequences is confirmed by S1 nuclease analysis of viral RNA labeled in vivo, in the presence of actinomycin D to inhibit host cell RNA transcription. The in vivo labeling of viral RNA, isolation of viral RNA's and S1 nuclease analysis of viral RNA is conducted as described by Rice, C. M. et al. (1987), Levis, R. et al. (1986) and Levis, R. et al (1987). S1 nuclease analysis of TSCAT and TRCAT-derived RNA vectors (e.g. viral RNA) uses the respective cDNA clones as unlabeled probe.

The time course analysis of CAT gene expression by TRCAT and TSCAT shows CAT activity to be detectable at 4 hours after transfection, increasing to a plateau by 16 to 20 hours post-transfection at 37° C. The amount of CAT made by TRCAT-derived Sindbis virus RNA vectors is found to be at least 2-3% of the total cell protein (based on CAT activity recovered from cells) and is comparable to the level of expression of Sindbis virus structural proteins, in infected cells, by Sindbis virus itself. A crude analysis of the amount of tPA produced at 20 hours post-transfection indicates production of at least $10^5$ molecules of tPA per transfected cell.

Replication of the Sindbis virus vectors containing CAT gene sequences is confirmed in all cell types tested. Specifically, in all systems subjected to replication analysis, except Toto2J1 and TotoCAT1, two RNA species are found, one that corresponds to the genome (e.g. co-migrates with the respective in vitro transcripts of the Sindbis virus clones) and a smaller species that corresponds exactly to the sizes expected of the respective subgenomic mRNA. Toto2J1 and TotoCAT1 are expected to give three RNA species due to the presence of two Sindbis virus junction regions. Two of the three RNA species are subgenomic RNA and one is a full-length molecule.

The ability of the Sindbis virus vectors of the present invention to provide the necessary replication and transcription functions of Sindbis virus is further demonstrated by analysis of cells transfected with TSCAT-ts-6. Specifically, when CEF's are transfected with TSCAT-ts-6, CAT gene expression, evidenced by positive CAT activity, occurs at 30° C., but not at 40° C.

It is further demonstrated that the rapid cessation of RNA synthesis due to the ts-6 mutation can be used to modulate the level of gene expression. Specifically, at various times (e.g. 0, 8, 12, 16 or 20 hours) after transfection with TSCAT-ts-6, cultures of CEF's are shifted up to and maintained at the non-permissive 40° C. temperature. Cells are then harvested at various times after the shift up to 40° C. and assayed for CAT activity as previously described. Early shifts to the non-permissive (40° C.) temperature are found to give lower subsequent CAT expression levels, as compared to expression of CAT at the permissive (30° C.) temperature. When the shift up to 40° C. is relatively late (e.g. 16-20) hours post-transfection, the levels of CAT expression exceed that at 30° C. Indeed, levels of CAT expression following a shift up to 40° C. at around 20 hours posttransfection even exceed TSCAT-derived vector production of CAT protein at 37° C. These results indicate that CAT mRNA is relatively stable and is translated more efficiently at 40° C. in CEF's.

then harvested for determination of virus yields and for further passaging. The cells are harvested at the same time and processed for CAT activity assays. Subsequent passages are identical to the first, except that the cells are not treated with DEAE-dextran, but are infected with 5 $\mu$l (passages 2-5) or 10 $\mu$l (passages 6-7) of media (diluted with 0.2 ml phosphate buffered saline plus 1% fetal calf serum) from the previous passage. After 1 hour at 37° C., 2 ml of fresh media is added and the cells incubated at 37° C. for 12 hours after which time the media and cells are individually harvested.

TABLE 1

Amplification of TRCAT by Passaging in the Presence of Sindbis Helper Virus

| Passage | Inoculum ($\mu$l)* | CAT activity (U) | Increase in CAT activity | Dilution§ | Amplification# |
|---|---|---|---|---|---|
| | Transfection, no virus | $1.1 \times 10^{-5}$ | | | |
| 1 | Transfection, + virus | $5.4 \times 10^{-6}$ | | 1 | |
| 2 | 5 | $6.7 \times 10^{-5}$ | 12 | $4.0 \times 10^{2}$ | $5.0 \times 10^{3}$ |
| 3 | 5 | $5.1 \times 10^{-4}$ | 94 | $1.6 \times 10^{5}$ | $1.5 \times 10^{7}$ |
| 4 | 5 | $1.2 \times 10^{-3}$ | 217 | $6.4 \times 10^{7}$ | $1.4 \times 10^{10}$ |
| 5 | 5 | $1.9 \times 10^{-3}$ | 343 | $2.6 \times 10^{10}$ | $8.8 \times 10^{12}$ |
| 6 | 10 | $3.4 \times 10^{-3}$ | 624 | $5.1 \times 10^{12}$ | $3.2 \times 10^{15}$ |
| 7 | 10 | $5.2 \times 10^{-3}$ | 967 | $1.0 \times 10^{15}$ | $9.9 \times 10^{17}$ |

*From a total volume of 2 ml of media harvested from the previous passage.
 Total CAT activity recovered from the infected monolayers at each passage. 1 U of CAT is defined as the amount of CAT that acetylates 1 $\mu$mol of chloramphenicol per minute at 37°. 1 U of CAT corresponds to 8 $\mu$g CAT protein, or $6 \times 10^{13}$ CAT tetramers (Shaw, W.V., 1975).
 Net increase in CAT activity = CAT activity at each passage/CAT activity at passage 1.
§Net dilution of media from passage 1.
The amplification is the net dilution of the media multiplied by the net increase in CAT activity at that passage.
 Sindbis virus is added at a multiplicity of infection of 0.5 at the time of transfection. The yield of virus at each passage is $5 \times 10^{9}$ to $1.2 \times 10^{10}$ plaque forming units, resulting in a moi of 6-30 for the subsequent passage.

EXAMPLE 5

Amplification and Packaging of Self-Replicating Sindbis Virus Vectors

This example demonstrates the ability of the self-replicating Sindbis virus vectors of the present invention, including the heterologous coding sequences contained therein, to be packaged in infectious virus particles. The ability to package the vectors, in turn, provides a means for amplifying both the number of vectors produced and for amplifying the level of expression of the heterologous coding sequences contained within the vectors.

As previously described, with the exception of Toto2J1 and TotoCAT1, the self-replicating Sindbis virus vectors detailed in the Examples herein have their structural genes replaced or rendered defective by the insertion of heterologous coding sequences and, thus, cannot synthesize the structural proteins needed to produce infectious virus particles. However, when Sindbis virus vector-transfected cells are also infected with wild-type Sindbis virus, infectious particles containing vector RNAs are produced.

As shown in Table 1, below, CAT activity is readily detectable when 0.25% to 0.5% of the total media (2 ml), from cell monolayers transfected with TSCAT or TRCAT-derived RNA vectors and coinfected with Sindbis virus, is used to infect new monolayers. Specifically, for the first passage, a semi-confluent monolayer ($1 \times 10^{6}$ cells) of CEFs is transfected with 1 $\mu$g TRCAT transcripts using the DEAE-dextran method and, at the same time, coinfected with Sindbis virus at a multiplicity of infection (moi) of 0.5, in a total volume of 0.2 ml. After 1 hour at 37° C., 2 ml of fresh media is added and the cultures then incubated for 12 hours. The media is As shown in Table 1, above, the TRCAT-derived vectors are stable for at least 7 passages ($10^{15}$ fold dilution of the media from the first passage) as determined by the expression of the CAT gene contained therein and by analysis of intracellular viral RNAs (see Rice, C. M. et al., 1987). Furthermore, the monolayer at the seventh passage gives about 1000 fold greater CAT expression than the transfected cells at the first passage. Thus, the net amplification of CAT activity is about $10^{18}$ fold during 7 passages. TRCAT derived vectors are, thus, readily packaged in infectious virus particles, are stable to passaging and efficiently amplified. Similarly, TSCAT-derived vectors give CAT expression and amplification for at least 6 passages in the presenct of Sindbis virus and TRtPA-derived vectors give tPA expression and amplification over a multiplicity of passages.

Unlike the aforementioned vectors, RNA transcripts made from Toto2J1 and TotoCAT1 clones constitute self-replicating and self-packaging Sindbis virus vectors. CEF's are transfected with RNA transcripts made from Sindbis virus clone Toto2J1 and TotoCAT1. The media from transfected cell cultures is then harvested, as described above, and used to infect normal CEF monolayers. The subsequently infected CEF monolayers are then assayed for both CAT gene expression and amplification of CAT gene expression. The efficient self-packaging, stability of the heterologous (e.g. CAT) gene insert and amplification of CAT gene expression is thereby achieved.

References

Ahlquist, P. et al. (1984) Proc. Nat'l Acad. Sci., U.S.A. 81:7066-7070.

Alton, N. K. and Vapnek, D. (1979) Nature 282:864-869.

Bailey, J. N. et al. (1983) *Proc. Nat'l Acad. Sci., U.S.A.* 80:2814–2818.
Burge, B. W. and Pfefferkorn, E. R. (1966a) *Virology* 30:204–213.
Burge, B. W. and Pfefferkorn, E. R. (1966b) *Virology* 30:214–223.
Butler, E. T. and Chamberlain, M. J. (1982) *J. Biol. Chem.* 257:5772–5778.
Dawson, W.O. et al (1986) *Proc Nat'l Acad. Sci., U.S.A.* 83:1832–1836.
Felgner, P. L. et al. (1987) *Proc. Nat'l Acad. Sci., U.S.A.* 84:7413.
Gorman, C. M. et al (1982) *Mol. Cell Biol.* 2:1044.
Granelli-Piperno and Reich (1978) *J. Exp. Med.* 148:223–234.
Hollifield et al. (1987) *Mol. Gen. Genet.* 210:248–255.
Kang, C. and Wu, C-W. (1987) *Nuc. Acids Res.* 15:2279–2294.
Konarska, M. M. et al. (1984) *Cell* 38:731–736.
Krieg, P. A. and Melton, D. A. (1984) *Nuc. Acids Res.* 12:7057–7070.
Leder, P. D. et al. (1977) *Science* 196:175–177.
Levis, R. et al. (1986) *Cell* 44:137.
Levis, R. et al. (1987) *Proc. Nat'l. Acad. Sci., U.S.A.* 84:4811.
Lutz, et al. (1987) *Proc. Nat'l. Acad. Sci., U.S.A.* 84:4379–4383.
Maniatis, T. et al. ed. (1982) *Molecular Cloning: A Laboratory Manual;* Cold Spring Harbor Laboratory, Cold Spring Harbor, N.Y.
Maxam, A. M. and Gilbert, W. (1980) *Methods in Enzymol.* 65:499–560.
Melton, D. A. et al. (1984) *Nucleic Acids Res.* 12:7035–7056.
Morris, C. E. et al. (1986) *Gene* 41:193.
Ou, J-H. et al. (1982) *Proc. Nat'l. Acad. Sci. U.S.A.* 79:5235–5239.
Pierce, J. S. et al. (1974) *Virology* 13:1030–1036.
Rice, C. M. et al. (1987) *J. Virology* 61:3809–3819.
Rice, C. M. and Strauss, J. H. (1981) *J. Mol. Biol.* 150:315–340.
Schlesinger, S. and Schlesinger, M. J. (1986) ed. *The Togaviridae and Flaviviridae,* Plenum Publishing Corp., N.Y.
Shaw, W. V. (1975) *Methods In Enzymol.* 53:737.
Stollar et al. (1967) Virology 33:650–658.
Strauss, E. G. and Strauss, J. H. (1980) *The Togaviruses,* R. W. Schlesinger, ed., Academic Press, N.Y., pp. 393–426.
Strauss, E. G. and Strauss, J. H. (1986) in *The Togaviridae and Flaviviridae,* Schlesinger, S. and Schlesinger, M. J., ed., Plenum Publishing Corp., N.Y., pp. 35–90.
Strauss, E. G. et al. (1984) *Virology* 133:92–110.
Strauss, E. G. et al. (1976) *Virology* 74:154–168.
van der Werf, S. et al. (1986) *Proc. Nat'l Acad. Sci., U.S.A.* 83:2330–2334.
Waller, E. K. (1984) Ph.D. Thesis "Tissue-Type Plasminogen Activators: Purification, Characterization, Molecular Cloning, Nucleotide Sequence and Regulation of Gene Expression" Rockefeller University, New York City, N.Y.
Weislander, L. (1979) *Anal. Biochem.* 98:305–309.
Zoller, M. J. and Smith, M. (1983) *Methods in Enzymol.* 100:468–500.

We claim:

1. A self-replicating and self-packaging recombinant Sindbis virus RNA molecule which comprises a heterologous coding sequence located upstream from the virus structural coding region and at least five nucleotides downstream from the start of the Sindbis virus subgenomic RNA, and a Sindbis virus junction region located upstream form the virus structural coding region and downstream form the heterologous coding sequence.

2. The Sindbis virus RNA molecule of claim 1, wherein the heterologous coding sequence encodes a protein of less than about 25 kilodaltons.

3. The Sindbis virus RNA molecule of claim 2 wherein the Sindbis virus junction region comprises the following sequence of nucleotides, reading from the 5'-end to the 3'-end of said sequence:

AUCUCUACGGUGGUCCUAAAUAGU

4. The Sindbis virus RNA molecule of claim 2 wherein the Sindbis virus junction region comprises the following sequence of nucleotides, reading from the 5'-end to the 3'-end of said sequence:

AUUACACCUGUCCUACU
GGCAUUGAGAACUUUUG
CCCAGAGCAAAAGAGCA
UUCCAAGCCAUCAGAGG
GGAAAUAAAGCAUCUCU
ACGGUGGUCCUAAAUAGU.

5. The Sindbis virus RNA molecule of claim 2 wherein the Sindbis virus junction region comprises the following sequence of nucleotides, reading from the 5'-end to the 3'-end of said sequence:

AUUACACCUGUCCUACU
GGCAUUGAGAACUUUUG
CCCAGAGCAAAAGAGCA
UUCCAAGCCAUCAGAGG
ACGGUGGUCCUAAAUAG
UCAGCAUAGU.

6. The Sindbis virus RNA molecule of claim 1 wherein the heterologous coding sequence is less than about 650 nucleotides in length.

7. The Sindbis virus RNA molecule of claim 6 wherein the Sindbis virus junction region comprises the following sequence of nucleotides, reading from the 5' end to the 3' end of said sequence:

AUCUCUACGGUGGUCCUAAAUAGU.

8. The Sindbis virus RNA molecule of claim 6 wherein the Sindbis virus junction region comprises the following sequence of nucleotides, reading from the 5' end o the 3' end of said sequence:

AUUACACCUGUCCUACU
GGCAUUGAGAACUUUUG
CCCAGAGCAAAAGAGCA
UUCCAAGCCAUCAGAGG
GGAAAUAAAGCAUCUCU
ACGGUGGUCCUAAAUAGU.

9. The Sindbis virus RNA molecule of claim 6 wherein the Sindbis virus junction region comprises the following sequence of nucleotides, reading from the 5' end to the 3' end of said sequence:

AUUACACCUGUCCUACU

-continued
```
GGCAUUGAGAACUUUUG
CCCAGAGCAAAAGAGCA
UUCCAAGCCAUCAGAGG
ACGGUGGUCCUAAAUAG
UCAGCAUAGU.
```

10. A DNA molecule which comprises DNA sequences encoding a Sindbis virus RNA molecule of claim 1, 2 or 6.

11. The DNA molecule of claim 10 wherein said DNA molecule is TotoCAT1.

12. A self-replicating and self-packaging recombinant Sindbis virus RNA molecule which comprises a heterologous coding sequence located downstream from the virus structural coding region and upstream from the first about 19 nucleotides immediately adjacent to and upstream from the viral polyA sequence.

13. The Sindbis virus RNA molecule of claim 12 wherein the heterologous coding sequence comprises a Sindbis virus junction region followed by an RNA sequence encoding a heterologous peptide of less than about 25 kilodaltons.

14. The Sindbis virus RNA molecule of claim 13 wherein the Sindbis virus junction region comprises the following sequence of nucleotides, reading from the 5'-end to the 3'-end of said sequence:

```
AUCUCUACGGUGGUCCUAAAUAGU
```

15. The Sindbis virus RNA molecule of claim 13 wherein the Sindbis virus junction region comprises the following sequence of nucleotides, reading from the 5'-end to the 3'-end of said sequence:

```
AUUACACCUGUCCUACU
GGCAUUGAGAACUUUUG
CCCAGAGCAAAAGAGCA
UUCCAAGCCAUCAGAGG
GGAAAUAAAGCAUCUCU
ACGGUGGUCCUAAAUAGU.
```

16. The Sindbis virus RNA molecule of claim 13 wherein the Sindbis virus junction region comprises the following sequence of nucleotides, reading from the 5'-end to the 3'-end of said sequence:

```
AUUACACCUGUCCUACU
GGCAUUGAGAACUUUUG
CCCAGAGCAAAAGAGCA
UUCCAAGCCAUCAGAGG
ACGGUGGUCCUAAAUAG
UCAGCAUAGU.
```

17. The Sindbis virus RNA molecule of claim 12 wherein the heterologous coding sequence comprises a Sindbis virus junction region followed by an RNA sequence of less than about 650 nucleotides in length.

18. The Sindbis virus RNA molecule of claim 17 wherein the Sindbis virus junction region comprises the following sequence of nucleotides, reading from the 5' end to the 3' end of said sequence:

```
AUCUCUACGGUGGUCCUAAAUAGU.
```

19. The Sindbis virus RNA molecule of claim 17 wherein the Sindbis virus junction region comprises the following sequence of nucleotides, reading from the 5' end to the 3' end of said sequence:

```
AUUACACCUGUCCUACU
GGCAUUGAGAACUUUUG
CCCAGAGCAAAAGAGCA
UUCCAAGCCAUCAGAGG
GGAAAUAAAGCAUCUCU
ACGGUGGUCCUAAAUAGU.
```

20. The Sindbis virus RNA molecule of claim 17 wherein the Sindbis virus junction region comprises the following sequence of nucleotides, reading from the 5' end to the 3' end of said sequence:

```
AUUACACCUGUCCUACU
GGCAUUGAGAACUUUUG
CCCAGAGCAAAAGAGCA
UUCCAAGCCAUCAGAGG
GGAAAUAAAGCAUCUCU
```

21. A DNA molecule which comprises DNA sequences encoding a Sindbis virus RNA molecule of claim 12, 13 or 17.

22. The DNA molecule of claim 21 wherein the DNA molecule is Toto2J1.

23. An infectious Sindbis virus particle containing a recombinant Sindbis virus RNA molecule of claim 1, 2, 3, 4, 5, 6, 7, 8, 9, 12, 13, 14, 15, 16, 17, 18, 19, or 20.

24. A transformed eucaryotic cell comprising a Sindbis virus RNA molecule of claim 1, 2, 3, 4, 5, 6, 7, 8, 9, 12, 13, 14, 15, 16, 17, 18, 19, or 20.

25. The eucaryotic cell of claim 24 wherein said cell is selected from the group of avian, insect and mammalian cells.

26. The eucaryotic cell of claim 25 wherein said cell is an avian cell.

27. A method for expressing a heterologous coding sequence in an eucaryotic host cell, comprising transfecting the host cell with the Sindbis virus RNA molecule of claim 1, 2, 3, 4, 5, 6, 7, 8, 9, 12, 13, 14, 15, 16, 17, 18, 19, or 20, and then growing the transfected host cell under conditions which allow for expression of the heterologous coding sequence.

28. The method of claim 27 wherein the host cell is selected from the group consisting of avian, insect and mammalian cells.

29. The method of claim 28 wherein the host cell is an avian cell.

30. The method of claim 27 further comprising the step of recovering infectious Sindbis virus particles produced by the transfected host cell.

31. The method of claim 30 wherein the host cell is selected form the group consisting of avian, insect and mammalian cells.

32. The method of claim 31 wherein the host cell is an avian cell.

* * * * *

UNITED STATES PATENT AND TRADEMARK OFFICE
CERTIFICATE OF CORRECTION

PATENT NO. : 5,217,879
DATED : June 8, 1993
INVENTOR(S) : Huang et al.

It is certified that error appears in the above-indentified patent and that said Letters Patent is hereby corrected as shown below:

In column 8, between lines 51-52, insert the following as a separate line:

GGAAAUAAAGCAUCUCU

In column 22, between lines 38-39, insert the following as a separate line:

GGAAAUAAAGCAUCUCU

In column 23, between lines 4-5, insert the following as a separate line:

GGAAAUAAAGCAUCUCU

In column 23, between lines 52-53, insert the following as a separate line:

GGAAAUAAAGCAUCUCU

In column 24, after line 25, insert the following as two separate lines:

ACGGUGGUCCUAAAUAG
UCAGCAUAGU

Signed and Sealed this

Fifth Day of July, 1994

Attest:

BRUCE LEHMAN

Attesting Officer      Commissioner of Patents and Trademarks